US012201618B2

United States Patent
Coric et al.

(10) Patent No.: US 12,201,618 B2
(45) Date of Patent: *Jan. 21, 2025

(54) USE OF RILUZOLE PRODRUGS TO TREAT ALZHEIMER'S DISEASE

(71) Applicant: Biohaven Therapeutics Ltd., New Haven, CT (US)

(72) Inventors: Vladimir Coric, Madison, CT (US); Robert Berman, New Haven, CT (US); Irfan Qureshi, Hackensack, NJ (US)

(73) Assignee: Biohaven Therapeutics Ltd., Tortola (VG)

( * ) Notice: Subject to any disclaimer, the term of this patent is extended or adjusted under 35 U.S.C. 154(b) by 801 days.

This patent is subject to a terminal disclaimer.

(21) Appl. No.: 17/151,577

(22) Filed: Jan. 18, 2021

(65) Prior Publication Data

US 2021/0212999 A1    Jul. 15, 2021

Related U.S. Application Data

(63) Continuation-in-part of application No. 17/261,057, filed as application No. PCT/US2019/042718 on Jul. 20, 2019.

(60) Provisional application No. 62/701,814, filed on Jul. 22, 2018.

(51) Int. Cl.
  *A61K 31/428*   (2006.01)
  *A61K 9/48*   (2006.01)
  *A61P 25/28*   (2006.01)

(52) U.S. Cl.
  CPC .............. *A61K 31/428* (2013.01); *A61K 9/48* (2013.01); *A61P 25/28* (2018.01)

(58) Field of Classification Search
  CPC .................................................. A61K 31/428
  See application file for complete search history.

(56) References Cited

U.S. PATENT DOCUMENTS

| 10,485,791 | B2 * | 11/2019 | Wrobel ............... A61K 31/496 |
| 10,639,298 | B2 * | 5/2020 | Wrobel ................ C07K 5/0812 |
| 10,905,681 | B2 * | 2/2021 | Wrobel ................... A61P 25/00 |
| 11,052,070 | B2 * | 7/2021 | Wrobel ................... A61P 25/00 |
| 2013/0064775 | A1 | 3/2013 | Busserolles et al. |
| 2018/0037557 | A1 | 2/2018 | Wrobel et al. |

FOREIGN PATENT DOCUMENTS

| WO | 2015089049 A1 | 6/2015 | |
| WO | WO-2016140879 A1 * | 9/2016 | ........... A61K 31/428 |
| WO | 2018031707 A1 | 2/2018 | |

OTHER PUBLICATIONS

International Search Report dated Nov. 12, 2019 issued for the corresponding application PCT/US2019/042718 (2 pages).
Written Opinion dated Nov. 12, 2019 issued for the corresponding application PCT/US2019/042718 (4 pages).
International Preliminary Report on Patentability dated Nov. 12, 2019, issued for the corresponding application PCT/US2019/042718 (5 pages).

* cited by examiner

*Primary Examiner* — Golam M Shameem

(57) ABSTRACT

Disclosed are methods of treating Alzheimer's Disease by administering to a patient in need thereof a riluzole prodrug such as troriluzole. Pharmaceutical compositions and kits including the riluzole prodrugs are also disclosed.

7 Claims, No Drawings

USE OF RILUZOLE PRODRUGS TO TREAT ALZHEIMER'S DISEASE

CROSS-REFERENCE TO RELATED APPLICATIONS

This application is a continuation-in-part of U.S. application Ser. No. 17/261,057 filed Jan. 18, 2021, which is a national stage application under 35 U.S.C. § 371 of International Application No. PCT/US2019/042718, filed Jul. 20, 2019, which claims priority to U.S. Provisional Application No. 62/701,814 filed Jul. 22, 2018, and all the benefits accruing therefrom under 35 U.S.C. § 119, the disclosure of each of which applications is herein incorporated by reference in its entirety.

FIELD OF THE INVENTION

The present invention relates to the use of prodrugs of riluzole to treat Alzheimer's disease.

BACKGROUND OF THE INVENTION

Alzheimer's disease is a progressive, fatal neurodegenerative dementia. It accounts for up to 80% of dementias. According to the Alzheimer's Association, in 2016 there were approximately 5.5 million people in the United States with the disease, and that number is expected to escalate rapidly in the coming years as the population ages. Reduced glutamate uptake transporters have been reported in post-mortem brain tissue of individuals with Alzheimer's disease and the level of glutamate transporter reduction correlates with cognitive impairment as well as markers of synaptic density and neurodegeneration.

The emotional and financial burden of AD to patients, family members, and society is enormous, and is predicted to grow exponentially as the median population age increases. The potential to preserve, or even improve, cognition in adults at high risk of cognitive decline due to AD clearly has important implications, not only for the affected individual, but also for the support system that bears the social and financial burdens of long-term caregiving.

There are medications currently approved for symptomatic treatment of AD, but they have small effect sizes and generally limited clinical benefits. An urgent need exists to find effective treatments for AD that can arrest or reverse the disease before its advanced stages. Therapeutic strategies aimed at restoring synaptic and extrasynaptic glutamate levels, offer potential therapeutic benefit in AD, in cognition, as well as in the neuroprotection of synapses, conferring the potential for disease modification. The significance of clinical research directed at this preclinically validated synaptic target cannot be overstated, given the lack of therapeutic progress in symptomatic and disease-modifying treatments since 2003.

The FDA originally approved riluzole (RILUTEK®) 50 mg twice-a-day (NDA #20-599) for the treatment of patients with amyotrophic lateral sclerosis (ALS). Riluzole is only indicated for ALS and has a number of non-desirable attributes that have limited its clinical use.

Riluzole tablets have 60% bioavailability, attributed to high first-pass metabolism in the liver. This is thought to be related to metabolism by the heterogeneously expressed CYP1A2 enzyme, which also accounts for the high PK variability associated with riluzole (Carlsson, 2000; Pittenger, 2015a, 2015b). In addition, riluzole is associated with reduced exposure when taken with meals (i.e. a negative food effect), resulting in the guidance to take riluzole within a three hour fast (one hour before or two hours after a meal).

Riluzole is also dosed twice a day, has dose-dependent effects on liver function tests and the drug substance itself has other intrinsic limitations including: very low solubility in water, poor oral palatability, pH dependent chemical stability, and intense oral numbness if administered directly to the oral mucosa.

Accordingly, new compounds, pharmaceutical compositions and methods are desired for the treatment of Alzheimer's Disease which may provide benefits for patients afflicted with the disease.

SUMMARY OF THE INVENTION

The present invention is directed to the treatment of Alzheimer's Disease with prodrugs of riluzole. By virtue of the present invention, it may now be possible to provide more effective AD treatments to patients. Patients may experience an improved response in one or more areas including, for example, overall survival, quality of life, overall response rate, duration of response, delay of onset, or patient reported outcome.

In one aspect of the invention, there is provided a method of treating AD in a patient in need thereof, comprising administering to the patient a therapeutically effective amount of a riluzole prodrug.

In one aspect, the riluzole prodrug has the following formula:

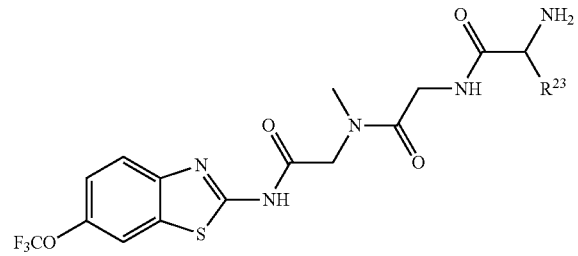

and pharmaceutically acceptable salts thereof, wherein:
$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$.

In one aspect, the riluzole prodrug has the following formula:

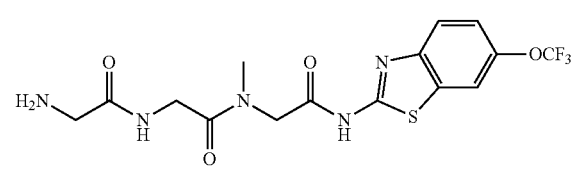 [SMILES: CN(CC(=O)Nc1nc2ccc(OC(F)(F)F)cc2s1)C(=O)CNC(=O)CN]

In one aspect, the riluzole prodrug is administered to the patient at a dosage of from about 100 to 400 mg per day.

In one aspect, the riluzole prodrug is administered to the patient at a dosage of about 110, or 140, or 150, or 210, or 280, or 350 mg per day.

In one aspect, the riluzole prodrug is administered to the patient at a dosage of 280 mg, once per day.

In one aspect, the riluzole prodrug is administered to the patient at a dosage of 140 mg, twice per day.

In one aspect, the riluzole prodrug is administered to the patient once per day.

In one aspect, the riluzole prodrug is administered to the patient twice per day.

In one aspect, the riluzole prodrug is administered to the patient in the form of a capsule.

In one aspect, the riluzole prodrug is administered to the patient in the form of a tablet.

In one aspect, the riluzole prodrug is administered to the patient for a duration of from about 8 weeks to 48 weeks. In one aspect, the riluzole prodrug is administered to the patient for a duration of from the onset of treatment to the end of the patient's life.

In one aspect of the invention, there is provided a method for improving a response in a patient afflicted with AD comprising administering to the patient in need thereof, an effective amount of a riluzole prodrug.

In one aspect, the improved response is one or more of overall survival, quality of life, overall response rate, duration of response, delay of onset, or patient reported outcome.

In one aspect of the invention, there is provided a kit for treating a patient afflicted with AD, the kit comprising:
(a) a riluzole prodrug; and
(b) instructions for administering the riluzole prodrug in the method of the invention.

In an aspect of the invention, there is provided a pharmaceutical composition in the form of a capsule comprising;

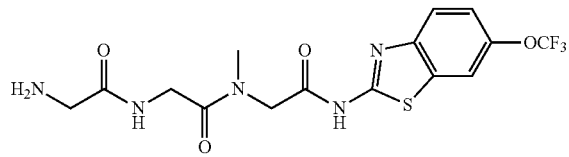 [SMILES: CN(CC(=O)Nc1nc2ccc(OC(F)(F)F)cc2s1)C(=O)CNC(=O)CN]

(troriluzole) as an active ingredient, and pharmaceutically acceptable excipients selected from mannitol, microcrystalline cellulose, dicalcium phosphate, hydroxypropyl cellulose, crospovidone, colloidal silicon dioxide and magnesium stearate.

In an aspect of the invention, the capsule comprises from about 40-50% troriluzole, 15-20% mannitol, 3-15% microcrystalline cellulose, 3-15% dicalcium phosphate, 5-10% hydroxypropyl cellulose, 5-10% crospovidone, 0.1-1% colloidal silicon dioxide and 0.1-1% magnesium stearate. The percentages are expressed as weight percent.

In an aspect of the invention, the capsule comprises from about 70-280 mg of troriluzole, preferably 140 mg of troriluzole, 60-90 mg of mannitol, 30-60 mg of microcrystalline cellulose, 5-20 mg of dicalcium phosphate, 5-10 mg of hydroxypropyl cellulose, 5-20 mg of crospovidone, 0.5-5 mg of colloidal silicon dioxide and 0.5-5 mg of magnesium stearate.

DETAILED DESCRIPTION OF THE INVENTION

The following detailed description is provided to aid those skilled in the art in practicing the present invention. Those of ordinary skill in the art may make modifications and variations in the embodiments described herein without departing from the spirit or scope of the present disclosure.

Unless otherwise defined, all technical and scientific terms used herein have the same meaning as commonly understood by one of ordinary skill in the art to which this disclosure belongs. The terminology used in the description is for describing particular embodiments only and is not intended to be limiting.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

The articles "a" and "an" refer to one or to more than one (i.e., to at least one) of the grammatical object of the article unless the context clearly indicates otherwise. By way of example, "an element" means one element or more than one element.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "administering" refers to the physical introduction of a composition comprising a therapeutic agent to a subject, using any of the various methods and delivery systems known to those skilled in the art. Typical routes of administration for riluzole prodrugs include oral administration, e.g., by capsule or tablet. Administering can also be performed, for example, once, a plurality of times, and/or over one or more extended periods and can be a therapeutically effective dose or a subtherapeutic dose.

The term "AUC" (area under the curve) refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals.

The term "Cmax" refers to a maximum concentration of a drug in blood, serum, a specified compartment or test area of a subject between administration of a first dose and administration of a second dose. The term Cmax could also refer to dose normalized ratios if specified.

The term "dosing interval," refers to the amount of time that elapses between multiple doses of a formulation disclosed herein being administered to a subject. Dosing interval can thus be indicated as ranges.

The term "dosing frequency" refers to the frequency of administering doses of a formulation disclosed herein in a given time. Dosing frequency can be indicated as the number of doses per a given time, e.g., once a week or once in two weeks.

The term "effective amount" refers to that amount which is sufficient to effect an intended result. The effective amount will vary depending on the subject and disease state being treated, the severity of the affliction and the manner of administration, and may be determined routinely by one of ordinary skill in the art.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

The term "pharmaceutically acceptable salt" refers to a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

The term "prodrug" refers to a precursor of a drug which may be administered in an altered or less active form. The prodrug may be converted into the active drug form in physiological environments by hydrolysis or other metabolic pathways. A discussion of prodrugs is provided in T. Higuchi and V. Stella, Pro-drugs as Novel Delivery Systems (1987) 14 of the *A.C.S. Symposium Series*, and in Bioreversible Carriers in Drug Design, (1987) Edward B. Roche, ed., American Pharmaceutical Association and Pergamon Press.

The terms "subject" and "patient" refer any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

The terms "therapeutically effective amount", "therapeutically effective dosage" and "therapeutically effective dose" of an agent (also sometimes referred to herein as a "drug") refers to any amount of the agent that, when used alone or in combination with another agent, protects a subject against the onset of a disease or promotes disease regression evidenced by a decrease in severity of disease symptoms, an increase in frequency and duration of disease symptom-free periods, or a prevention of impairment or disability due to the disease affliction. The therapeutically effective amount of an agent can be evaluated using a variety of methods known to the skilled practitioner, such as in human subjects during clinical trials, in animal model systems predictive of efficacy in humans, or by assaying the activity of the agent in in vitro assays.

The term "Tmax" refers to a time or period after administration of a drug when the maximum concentration (Cmax) is reached in blood, serum, a specified compartment or test area of a subject.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

Riluzole is currently available in the market as RILUTEK® (riluzole) is available from Sanofi-Aventis, Bridgewater, N.J. and has the structure shown below.

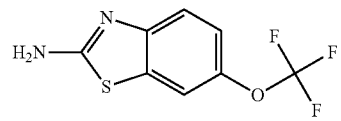

6-(trifluoromethoxy)benzothiazol-2-amine

Certain preferred riluzole prodrugs for use in accordance with the present invention have the structure:

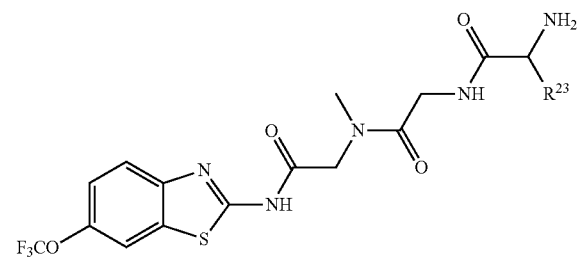

including enantiomers, diastereomers, hydrates, solvates, pharmaceutically acceptable salts, and complexes thereof, wherein:

$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$. Such agents may be useful as part of the combination of the present invention.

One especially preferred riluzole prodrug, troriluzole, has the following formula:

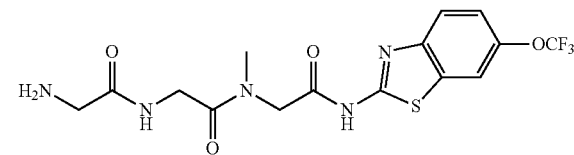 [SMILES: CN(CC(=O)Nc1nc2ccc(OC(F)(F)F)cc2s1)C(=O)CNC(=O)CN]

Prodrugs of riluzole are described, for example, in U.S. Pat. No. 9,725,427, issued Aug. 8, 2017, U.S. patent application Ser. No. 14/410,647, filed Dec. 23, 2014, U.S. patent application Ser. No. 15/549,154, filed Aug. 5, 2017, PCT Application Serial No. PCT/US2016/019773, filed Feb. 26, 2016, and PCT Application Serial No. PCT/US2016/019787, filed Feb. 26, 2016.

The riluzole prodrugs may be present as isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, Cl and I. Various isotopically labeled compounds of the present disclosure, for example those into which radioactive isotopes such as $^3$H, $^{13}$C and $^{14}$C are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, or hydrates, as the case may be.

In some variations, the compounds disclosed herein may be varied such that from 1 to "n" hydrogens attached to a carbon atom is/are replaced by deuterium, in which "n" is the number of hydrogens in the molecule. Such compounds may exhibit increased resistance to metabolism and are thus useful for increasing the half life of the compound when administered to a subject. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved drug metabolism and pharmacokinetics (DMPK) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out the procedures known to those skilled in the art by substituting a readily available isotopically labeled reagent for a non-isotopically labeled reagent. It is understood that deuterium in this context is regarded as a substituent in the compounds provided herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as 'H' or "hydrogen", the position is understood to have hydrogen at its natural abundance isotopic composition.

The riluzole prodrugs of the present invention may be given orally, sublingually, intranasally, buccally, subcutaneously or in any other suitable means of delivery.

The dose of the riluzole prodrug to be administered may depend on the subject to be treated inclusive of the age, sex, weight and general health condition thereof. In this regard, precise amounts of the agent(s) for administration will depend on the judgment of the practitioner. In determining the effective amount of the riluzole prodrug to be administered in the treatment or reducing of the conditions associated with the symptoms and disorders, the physician may evaluate clinical factors including symptoms severity or progression of the disorder. The effective amount of the treatment will vary depending on the subject and disease state being treated, the severity of the affliction and the manner of administration, and may be determined routinely by one of ordinary skill in the art.

The riluzole prodrug for treating AD or symptoms may be dosed at any dose effective to treat AD with a tolerable amount of side effects, if any, for the particular patient being treated. Typical dosage frequencies for the riluzole prodrugs include once a day, twice a day, three times a day, four times a day, once every other day, once a week, twice a week, three times a week, four times a week, once every two weeks, once or twice monthly, and the like. Examples of dosages include at or below about 400 mg/day, at or below about 300 mg/day, at or below about 150 mg/day, at or below about 100 mg/day, at or below about 70 mg/day, at or below about 60 mg/day, at or below about 50 mg/day, at or below about 42.5 mg/day, at or below about 37.5 mg/day at or below about 35 mg/day, at or below about 20 mg/day, at or below about 17.5 mg/day, at or below about 15 mg/day, at or below about 10 mg/day, at or below about 5 mg/day, or at or below about 1 mg/day. In one aspect, the riluzole prodrug is administered to the patient at a dosage of from about 110, or 140, or 150, or 210, or 280, or 350 mg per day. In one aspect, the riluzole prodrug is administered to the patient at a dosage of 280 mg, once per day. In another aspect, the riluzole prodrug is administered to the patient at a dosage of 140 mg, twice per day.

The pharmaceutical compositions of the present invention comprising the riluzole prodrug typically also include other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook of Pharmaceutical Excipients, fifth edition, 2005 edited by Rowe et al., McGraw Hill) and have been utilized to yield a novel sublingual formulation with unexpected properties.

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinyl-pyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. The compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in conventional methods known in the art, for example, by means of conventional mixing, dissolving, granulating, dragee-making, levigating, emulsifying, encapsulating, entrapping, lyophilizing processes and the like.

In one aspect of the invention, the riluzole prodrug is provided in a form of an orally dissolving or disintegrating tablet (ODT) for sublingual administration. In general, the excipients, including mannitol and gelatin, are blended, solubilized with water and deaerated before being mixed with the active pharmaceutical ingredient (API), which has been milled separately. The particle size of the API (D50) is less preferably than about 2 microns. The mixture is lyophilized by flash freezing and then freeze-dried. The effective amount of riluzole prodrug for the sublingual formulation useful in the present invention to achieve a therapeutically effective dose may be less than that of orally administered agent. For example, the effective dose of the sublingual formulation of the riluzole prodrug may be about 1 to 95%, preferably 50 to 90%, more preferably 70 to 85% and most preferably about 80% of that of the orally administered agent in a conventional tablet or capsule. In one aspect of the invention, the pharmaceutical compositions are prepared in an ODT form as described in U.S. Pat. No. 9,192,580, issued Nov. 24, 2015. ODT dosage forms are further described by Gregory et al., U.K. Patent No. 1,548,022 using fish gelatin as the carrier. Fish gelatins suitable for use in the invention are commercially available.

Typically, the ODT dosage form disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration.

The ODT compositions according to the invention can also contain, in addition to the active ingredient arid fish gelatin carrier, other matrix forming agents and secondary components. Matrix forming agents suitable for use in the present invention include materials derived from animal or vegetable proteins, such as other gelatins, dextrins and soy, wheat and psyllium seed proteins; gums such as acacia, guar, agar, and 10 xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other materials which may also be incorporated into the ODT compositions of the present invention include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine. One or more matrix forming agents may be incorporated into the solution or suspension prior to solidification (freezing). The matrix forming agent may be present in addition to a surfactant or to the exclusion of a surfactant. In addition to forming the matrix, the matrix forming agent may aid in maintaining the dispersion of any active ingredient within the solution of suspension. This is especially helpful in the case of active agents that are not sufficiently soluble in water and must, therefore, be suspended rather than dissolved. Secondary components such as preservatives, antioxidants, surfactants, viscosity enhancers, coloring agents, flavoring agents, pH modifiers, sweeteners or taste-masking agents may also be incorporated into the fast-dissolving compositions. Suitable coloring agents include red, black and yellow iron oxides and FD & C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include the edible acids and bases, such as citric acid, tartaric acid, phosphoric acid, hydrochloric acid, maleic acid and sodium hydroxide. Suitable sweeteners include, for example, sucralose, aspartame, acesulfame K and thaumatin. Suitable taste-masking agents include, for example, sodium bicarbonate, ion exchange resins, cyclodextrin inclusion compounds, adsorbates or microencapsulated actives.

In a preferred aspect of the invention, the ODT compositions comprises from about 50-70 wt % riluzole prodrug, about 10-30 wt % fish gelatin, about 10-20 wt % of one or more fillers, and 0.1-5.0 wt % of one or more flavorants.

Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993,674; 8,048,449; 8,127,516; 8,158,152; 8,221,480; 8,256,233; and 8,313,768.

In a preferred aspect of the invention, there is provided a pharmaceutical composition in the form of a capsule comprising;

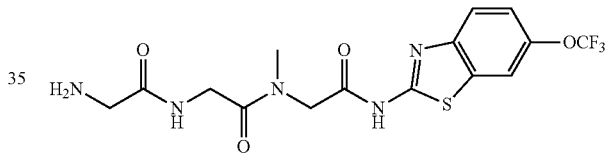

(troriluzole) as an active ingredient, and pharmaceutically acceptable excipients selected from mannitol, microcrystalline cellulose, dicalcium phosphate, hydroxypropyl cellulose, crospovidone, colloidal silicon dioxide and magnesium stearate. In an aspect of the invention, the capsule comprises from about 40-50% troriluzole, 15-20% mannitol, 3-15% microcrystalline cellulose, 3-15% dicalcium phosphate, 5-10% hydroxypropyl cellulose, 5-10% crospovidone, 0.1-1% colloidal silicon dioxide and 0.1-1% magnesium stearate. The percentages are expressed as weight percent. In an aspect of the invention, the capsule comprises from about 70-280 mg of troriluzole, preferably 140 mg of troriluzole, 60-90 mg of mannitol, 30-60 mg of microcrystalline cellulose, 5-20 mg of dicalcium phosphate, 5-10 mg of hydroxypropyl cellulose, 5-20 mg of crospovidone, 0.5-5 mg of colloidal silicon dioxide and 0.5-5 mg of magnesium stearate. Techniques for manufacturing capsules suitable for use in accordance with the present invention are known to those skilled in the art.

In an embodiment, provided is a method of treating mild Alzheimer's Disease in a patient in need thereof, which includes administering to the patient a therapeutically effective amount of a riluzole prodrug. Mild Alzheimer's Disease is an early stage Alzheimer's Disease, where a person may still function independently. She or he may drive, work and be part of social activities. Despite this, the person may feel as if she or he is having memory lapses, such as forgetting familiar words or the location of everyday objects. Symptoms may not be widely apparent at this stage, but family and close friends may take notice and a doctor would be able to identify symptoms using certain diagnostic tools. Common difficulties may include coming up with the right word or name, remembering names when introduced to new people, having difficulty performing tasks in social or work settings, forgetting material that was just read, losing or misplacing a valuable object, and experiencing increased trouble with planning or organizing. More information about the stages of Alzheimer's Disease may found at https://www.alz.org/alzheimers-dementia/stages.

Also within the scope of the present invention are kits comprising a riluzole prodrug (e.g., troriluzole) for therapeutic uses. Kits typically include a label indicating the intended use of the contents of the kit and instructions for use. The term label includes any writing, or recorded material supplied on or with the kit, or which otherwise accompanies the kit.

EXAMPLES

The following examples illustrate the invention and are not intended to limit the scope of the invention.

Example 1

A clinical study is conducted with the following parameters. For additional information, refer to ClinicalTrials.gov Identifier NCT03605667, www.clinicaltrials.gov.

Study Description
Brief Summary

Preclinical models suggest that riluzole, the active metabolite of BHV-4157, may protect from AD-related pathology and cognitive dysfunction. Titrated dose of BHV-4157 to 280 mg, or placebo, taken orally once daily. Duration of treatment is 48 weeks. There is also a screening period of up to 42 days; and a 4-week post-treatment observation period.

| Condition or disease | Intervention/treatment | Phase |
|---|---|---|
| Alzheimer Disease | Drug: troriluzoleDrug: Placebo oral capsule | Phase 2/ Phase 3 |

| Study Design | |
|---|---|
| Study Type: | Interventional (Clinical Trial) |
| Estimated Enrollment: | 292 participants |
| Allocation: | Randomized |
| Intervention Model: | Parallel Assignment |
| Masking: | None (Open Label) |
| Primary Purpose: | Treatment |
| Official Title: | A Phase 2 Randomized Double-Blind Placebo-Controlled Trial to Evaluate the Efficacy and Safety of BHV-4157 in Patients With Mild to Moderate Alzheimer's Disease |

| Arms and Interventions | |
|---|---|
| Arm | Intervention/treatment |
| Experimental: BHV-4157 troriluzole, 280 mg | Drug: troriluzole Oral BHV-4157 will be given |
| capsules, QD | daily for up to 48 weeks Other Name: BHV-4157 |
| Placebo Comparator: Placebo matching 280 mg placebo capsules, QD | Drug: Placebo oral capsule Oral matching placebo will be given daily for up to 48 weeks |

Outcome Measures
Primary Outcome Measures:
 1. The change in Alzheimer's Disease Assessment Scale Cognitive Subscale (ADAS-Cog 11) from baseline to week 48 between the BHV-4157 treatment group and the placebo group [Time Frame: Baseline to Week 48]

Alzheimer's Disease Assessment Scale Cognitive Subscale (ADAS-Cog 11)

The ADAS-Cog 11 evaluates memory (word recall, word recognition), reasoning (following commands), language (naming, comprehension), orientation, ideational praxis (placing a letter in an envelope) and constructional praxis (copying geometric designs). Ratings of spoken language, language comprehension, word finding difficulty, and ability to remember test instructions are also obtained. The test is scored in terms of errors, with higher scores reflecting poorer performance and greater impairment. Scores can range from 0 (best) to 70 (worse).

| Eligibility Criteria | |
|---|---|
| Ages Eligible for Study: | 50 Years to 85 Years (Adult, Older Adult) |
| Sexes Eligible for Study: | All |
| Accepts Healthy Volunteers: | No |

Criteria
Key Inclusion Criteria:
 Age 50 to 85 (inclusive) at screening
 Diagnosed with probable Alzheimer's disease dementia: Core clinical criteria in accordance with NIA/Alzheimer's Association Guidelines.
 Living in the community (includes assisted living facilities, but excludes long-term care nursing facilities).
 Ambulatory, or able to walk with an assistive device, such as a cane or walker.
 Participants must have a study partner who has frequent interaction with them (approximately >3-4 times per week), will be present for all clinic visits, and can assist in compliance with study procedures.
 A brain MRI scan within 6 months of screening consistent with a diagnosis of Alzheimer's disease.
 Participants should be treated with a stable dosage regimen of FDA-approved AD medications (acetylcholinesterase inhibitors (AchEI) and/or memantine) for at least 3 months prior to screening. Participants should be expected to remain on a stable dosage regimen of these medications for the duration of the trial.
 Participants who are not being treated with FDA-approved AD medications at the time of screening, because they have contraindications to these medications, or because they have previously failed treatment with these medications, are also eligible for inclusion, if it is expected that they will not be treated with these medications for the duration of the trial.

Key Exclusion Criteria:

Hepatic impairment defined as Child-Pugh class of A or more severe liver impairment.

Other neurodegenerative diseases and causes of dementias, including Parkinson's disease and Huntington's disease, vascular dementia, CJD (Creutzfeldt-Jakob disease), LBD (Lewy Body dementia), PSP (Progressive Supranuclear Palsy), AIDS (Acquired Immunodeficiency Syndrome), or NPH (normal pressure hydrocephalus).

History of a major depressive episode within the past 6 months of screening.

Insulin-dependent diabetes or uncontrolled diabetes with HbA1c value >8.0%.

Cancer or a malignant tumor within the past 3 years, except patients who underwent potentially curative therapy with no evidence of recurrence for >3 years. Patients with stable prostate cancer or non-melanoma skin cancers are not excluded.

Participation in another clinical trial for an investigational agent and having taken at least one dose of study medication, unless confirmed as having been on placebo, within 12 weeks prior to screening. The end of a previous investigational trial is defined as the date of the last dose of an investigational agent.

Example 2

A clinical study is conducted with the following parameters.

| STUDY SUMMARY | |
|---|---|
| Title | A Phase 2 Randomized Double-Blind Placebo-Controlled Trial to Evaluate the Efficacy and Safety of BHV-4157 in Patients with Mild to Moderate Alzheimer's Disease |
| Rationale | BHV-4157 is a new chemical entity 3rd-generation prodrug of the glutamate modulator, riluzole, which has been designed to bypass first-pass metabolism therein providing greater bioavailability, diminished PK variability, lower hepatic burden, lack of food effect, longer half-life and once daily dosing. Preclinical models suggest that riluzole, the active metabolite of BHV-4157, may protect from AD-related pathology and cognitive dysfunction. |
| Target Population | Male and females, age 50 to 85 years (inclusive at screening), diagnosed with Alzheimer's Disease (in accordance with NIA/Alzheimer's Association Guidelines) of mild to moderate severity including MMSE score 14-24 at the screening visit. Eligible participants should be receiving a stable dose of FDA-approved AD medication(s) (acetylcholinesterase inhibitors (AchEI) and/or memantine) for at least 3 months prior to screening and willing to remain on same dose(s) for trial duration. Those participants with contraindications or failed treatment with either AchEI and/or memantine will be eligible for inclusion. |
| Number of Participants | Approximately 292 participants will be randomly allocated using a 1:1 allocation to active treatment or placebo. |
| Drug Dosage & Treatment Duration | Titrated dose of BHV-4157 to 280 mg, or placebo, taken orally once daily. Duration of treatment is 48 weeks. There is also a screening period of up to 42 days; and a 4-week post-treatment observation period. |
| Objectives | The primary objective is to: evaluate the efficacy of BHV-4157 as measured by the ADAS-Cog 11. The key secondary objective is to: evaluate the efficacy of BHV-4157 as measured by the CDR-Sum of Boxes. The secondary objectives are to: (1) evaluate the efficacy of BHV-4157 as measured by: Quarc volumetric MRI (bilateral hippocampal volume, bilateral lateral ventricles, and whole brain volume), Neuropsychiatric Inventory (NPI), ADCS-ADL, neuropsychological test battery (Craft Story 21 Recall (Immediate & Delayed), Benson Figure (Copy & Delayed Recall), Multilingual Naming Test (MINT), Letter & Category Fluency, Trail Making Test A & B, Number Span Forward & Backward), Mini-Mental State Examination (MMSE), and Montreal Cognitive Assessment (MoCA); (2) evaluate the safety and tolerability of BHV-4157 as measured by mortality rates, serious adverse events, adverse events, clinical safety laboratories, physical examinations and significant ECG changes. Exploratory objectives are to: (1) assess pharmacokinetics of BHV-4157 (2) assess treatment response in participants with typical vs. atypical Alzheimer's disease presentation as well as by Apo E genotype; (3) evaluate a panel of CSF, serum and plasma biomarkers (A$\beta$42, A$\beta$42/40 ratio, total tau, p-tau, neurogranin, NfL, YKL-40, VILIP, SNAP-25, sTREM2) in a subset of the study population (estimated n = 50 active, n = 50 placebo) at screening, week 24 and week 48. |
| Study Design & Statistical Plan | This is a phase 2 multi-center, randomized, double blind, placebo-controlled, parallel group study. MMSE score (14 to 19; 20 to 24) at screening and Site will be stratification factors. An Interim Futility Analysis for proof-of-concept will be conducted when a sentinel cohort consisting of the first 50 randomized participants in each arm has received 24 weeks of treatment or longer on study (completers only analysis). At this point, an interim data freeze (database snapshot) will take place and the analyses will be conducted using the frozen data set. The study will continue if any one of the following conditions is met, using a one-sided test at the stated significance level: Mean change from baseline to interim analysis on ADAS-Cog 11: Treatment - Control is significantly improved at the $p \leq 0.50$ level. Mean change from screening to interim analysis on MRI Quarc hippocampal volume: Treatment - Control is significantly improved at the $p \leq 0.20$ level. |

| | STUDY SUMMARY |
|---|---|
| | If both conditions fail, the DSMB will indicate that futility criteria have been met to the Study Steering Committee (SSC) who are overseeing the trial. The SSC will have the final responsibility for the decision to stop the trial.<br>This interim analysis is designed to stop with a probability of 40% under the assumption that the two endpoints are independent and that there is no true difference between arms in both of the interim measures above.<br>Overall study power at the final analysis:<br>Given that the interim analysis has power of 86%, and that the interim and final endpoints have correlation of at least 20%, the overall study has 80% power to detect a difference of 2.5 points on the ADAS-Cog 11 at week 48 (SD 6 points), at two-sided 5% significance level.<br>At the final analysis, there is also 80% power to detect a mean increase of 0.9 points on CDR-SOB (key secondary endpoint) at 48 weeks, which corresponds to a decline in the active arm of about 40% or less of the placebo arm decline.<br>The primary and key secondary endpoints at the final analysis will be tested using a hierarchical gatekeeper strategy: if ADAS-Cog 11 is significant at the 5% level, then CDR-SOB will also be tested at 5% significance level. If both primary and key secondary outcomes are significant, the remainder of the secondary outcomes will be tested at overall 5% significance level using a Holm's step down test. This will preserve alpha at 5% overall for all endpoints tested.<br>Statistical methods:<br>Both the interim and final analysis will use a mixed effects repeated measures model. |
| Primary Endpoint | The change in ADAS-Cog 11 from baseline to week 48 between the BHV-4157 treatment group and the placebo group. |
| Secondary Endpoints | The change in CDR-Sum of Boxes from baseline to week 48 between the BHV-4157 treatment group and the placebo group.<br>The change in MRI Quarc bilateral hippocampal volume, bilateral lateral ventricles, and whole brain volume from screening to week 48.<br>The change in the NPI total score from baseline to weeks 24 and 48.<br>The change in ADCS-ADL from baseline to weeks 24 and 48.<br>The change in composite score from baseline to week 48 on the neuropsychological test battery (Craft Story 21 Recall (Immediate & Delayed), Benson Figure (Copy & Delayed Recall), Multilingual Naming Test (MINT), Letter & Category Fluency, Trail Making Test A & B, Number Span Forward & Backward).<br>The change in MMSE from baseline to weeks 24 and 48.<br>The change in MoCA scores from baseline to weeks 24 and 48.<br>The change in safety and tolerability measures including: (1) adverse events; (2) clinical laboratory tests; (3) vital signs; (4) physical examinations; (5) ECGs. |

LIST OF ABBREVIATIONS

Aβ β-Amyloid
AchEI Acetylcholinesterase Inhibitor
AD Alzheimer's Disease
ADAS-Cog Alzheimer's Disease Assessment Scale-Cognitive (subscale)
ADCS-ADL Alzheimer's Disease Cooperative Study-Activities of Daily Living Inventory
ADME Absorption, Distribution, Metabolism, Excretion
AICD Automatic Implanted Cardioverter Defibrillator
AUC Area Under the Curve
AE Adverse Event
AIDS Acquired Immunodeficiency Syndrome
ALS Amyotrophic Lateral Sclerosis
ALT Alanine Aminotransferase
ApoE Apolipoprotein E
AST Aspartate Aminotransferase
BDNF Brain-derived Neurotrophic Factor
BID Twice per day
BUN Blood Urea Nitrogen
CDR-SOB Clinical Dementia Rating Sum of Boxes
CFR Code of Federal Regulations
CJD Creutzfeldt-Jakob Disease
CONSORT Consolidated Standards of Reporting Trials
CPK Creatinine Phosphokinase
CSF Cerebrospinal Fluid
CYP Cytochrome P450
DMP Data Management Plan
DSM Diagnostic and Statistical Manual of Mental Disorders
DSMB Data Safety & Monitoring Board
eCRF Electronic Case Report Form
ECG Electrocardiogram
EDC Electronic Data Capture
FDA Food & Drug Administration
GCP Good Clinical Practice
GGT Gamma-Glutamyl Transferase
GMP Good Manufacturing Practice
HCV Hepatitis C Virus
HDL High-Density Lipoprotein
HIPAA Health Insurance Portability & Accountability Act
hr (unit) Hour
ICF Informed Consent Form
ICH International Conference on Harmonization
IRB Institutional Review Board
ITT Intent-To-Treat
kg (unit) Kilogram
LAR Legally Authorized Representative
LBD Lewy Bodies Dementia
LDH Lactate Dehydrogenase
LDL Low-Density Lipoprotein
LFT Liver Function Test
LP Lumbar Puncture
MAD Multiple Ascending Dose
MCI Multiple Cerebral Infarctions
MINT Multi-lingual Naming Test
mITT Modified Intent-To-Treat mg (unit) Milligram
ml (unit) Milliliter
MMSE Mini-Mental State Examination
MoCA Montreal Cognitive Assessment
MRI Magnetic Resonance Imaging
NfL Neurofilament Light (Protein)
ng (unit) Nanogram
NIA National Institute on Aging
NOAEL No-observed-adverse-effect-level
NPH Normal Pressure Hydrocephalus
NPI Neuropsychiatric Inventory
OHRP Office of Human Research Protection
PHI Personal Health Information
PI Principal Investigator
PK Pharmacokinetic
PP Per Protocol
PSP Progressive Supranuclear Palsy
QD Once per day
Quarc Quantitative Anatomical Regional Change
RBC Red Blood Cell
SAD Single Ascending Dose
SAE Serious Adverse Event
SAP Statistical Analysis Plan
SCA Spinocerebellar Ataxia
SD Standard Deviation
SSC Study Steering Committee
sTREM2 Soluble Variant Triggering Receptor Expressed on Myeloid Cells 2
ULN Upper Limit of Normal
USPI United States Prescribing Information
VILIP Visinin-Like Protein
vMRI Volumetric Magnetic Resonance Imaging
WBC White Blood Cell 1 Study Design This is a phase 2 multi-center, randomized, double blind, placebo-controlled, parallel group study in patients with mild to moderate Alzheimer's disease.

Participants will be randomized to one of two groups: 280 mg of BHV-4157 or placebo. The BHV-4157 treatment dose of 280 mg was selected for evaluation in the current study based on evidence summarized in Section 1.8. Treatment duration is 48 weeks (12 months). There is a screening period of up to 42 days and a 4-week post-treatment observation period.

An interim analysis for futility will be conducted when a sentinel cohort consisting of the first 50 randomized participants in each arm has received 24 weeks of treatment or longer on study (completers only analysis). The interim analysis is based on the change, from baseline to week 24, of two measures, including: the surrogate primary endpoint (ADAS-Cog 11) and hippocampal volume change.

2 Objectives 2.1 Primary Objective

The primary objective is to evaluate the efficacy of BHV-4157 as measured by ADAS-Cog 11.

2.2 Secondary Objectives

The secondary objectives are to evaluate the efficacy, safety and tolerability of BHV-4157 as outlined below.

2.2.1 Efficacy

The efficacy of BHV-4157 will be assessed by the following measures:
 CDR-Sum of Boxes (key secondary objective),
 Volumetric MRI (Quarc bilateral hippocampal volume, bilateral lateral ventricles, and whole brain volume),
 Neuropsychiatric Inventory (NPI),
 Alzheimer's Disease Cooperative Study (ADCS)-Activities of Daily Living (ADCS-ADL),
 Neuropsychological test battery (Craft Story 21 Recall (Immediate & Delayed), Benson Complex Figure (Copy & Delayed Recall), Multi-lingual Naming Test (MINT), Letter & Category Fluency, Trail Making Test A & B, Number Span Forward and Backward),
 Mini-Mental State Examination (MMSE), and
 Montreal Cognitive Assessment (MoCA).

2.2.2 Safety and Tolerability

The safety and tolerability of BHV-4157 will be assessed by the following measures:
 Mortality rates,
 Serious adverse event rates,
 Adverse events,
 Clinical safety laboratories,
 Vital signs,
 Physical examinations,
 ECGs, and
 Use of concomitant medications.

3 Endpoints 3.1 Primary Endpoint

The primary efficacy endpoint is the within-participant change in ADAS-Cog 11 from baseline to week 48, compared between the treatment group and the placebo group.

3.2 Secondary Endpoints

The secondary endpoints will measure the efficacy, and safety and tolerability of BHV-4157 as outlined below.

3.2.1 Efficacy

The efficacy of BHV-4157 will be assessed by the within-participant changes from baseline to week 48, compared between the treatment group and the placebo group, on the following:
 CDR-Sum of Boxes (key secondary endpoint),
 Volumetric MRI (Quarc bilateral hippocampal volume, bilateral lateral ventricles, and whole brain volume)
 Neuropsychiatric Inventory (NPI) scores
 Alzheimer's Disease Cooperative Study (ADCS)-Activities of Daily Living (ADCS-ADL) scores
 Neuropsychological test battery scores (Craft Story 21 Recall (Immediate & Delayed), Benson Complex Figure (Copy & Delayed Recall), Multi-lingual Naming Test (MINT), Letter & Category Fluency, Trail Making Test A & B, Number Span Forward and Backward),
 Mini-Mental State Examination (MMSE) scores, and
 Montreal Cognitive Assessment (MoCA) scores.

3.2.2 Safety and Tolerability

The following safety and tolerability measures will be assessed for differences between the treatment group and the placebo group:
 Occurrence of mortality events,
 Occurrence of serious adverse events (SAEs),
 Occurrence of adverse events (AEs),
 Clinical laboratory tests,
 Vital signs,
 Physical examinations,
 ECGs, and
 Use of concomitant medications.

4 Study Drug 4.1 Study Medication

The study medication will be presented as one of the following:
 BHV-4157, 1 or 2 capsules (size 1) of 140 mg each, depending on assigned dose
 1 or 2 capsules of matching Placebo The study medication capsule should not be opened.

The study medication will be securely stored at the study site in accordance with the conditions specified on the label, separately from other drugs. The study medication may not be used for any purpose other than this study.

4.2 Blinding

This is a double-blind placebo-controlled trial. Treatments will be blinded to the participants and study personnel throughout the study. Treatment blind will be maintained by use of matching placebo medication.

Only in the case of an emergency, when knowledge of whether the participant has received the investigational product is essential for the clinical management or welfare of the participant, may the Investigator unblind a participant's treatment assignment. Procedures for emergency unblinding are initiated by contacting the ADCS Medical Monitor.

5 Patient Selection 5.1 Inclusion Criteria

Participants must meet all of the following inclusion criteria to be eligible for enrollment:
1. Age 50 to 85 (inclusive) at screening
2. Diagnosed with probable Alzheimer's disease dementia: Core clinical criteria in accordance with NIA/Alzheimer's Association Guidelines.
3. Living in the community (includes assisted living facilities, but excludes long-term care nursing facilities).
4. Ambulatory, or able to walk with an assistive device, such as a cane or walker.
5. Participants must have a study partner who has frequent interaction with them (approximately >3-4 times per week), will be present for all clinic visits, and can assist in compliance with study procedures.
6. Female patients must be post-menopausal for at least 2 consecutive years or surgically sterile (bilateral tubal ligation, hysterectomy or bilateral oophorectomy) for at least 6 months prior to screening.
7. A modified Hachinski score of 4 or less at screening.
8. An MMSE score of 14 to 24, inclusive, at screening.
9. A brain MRI scan within 6 months of screening consistent with a diagnosis of Alzheimer's disease.
10. Body mass index (BMI) 35 kg/m$^2$ at screening.
11. Participants should be treated with a stable dosage regimen of FDA-approved AD medications (acetylcholinesterase inhibitors (AchEI) and/or memantine) for at least 3 months prior to screening. Participants should be expected to remain on a stable dosage regimen of these medications for the duration of the trial.
    a. Participants who are not being treated with FDA-approved AD medications at the time of screening, because they have contraindications to these medications, or because they have previously failed treatment with these medications, are also eligible for inclusion, if it is expected that they will not be treated with these medications for the duration of the trial.
12. Ability (patients and their study partners) to read, speak and understand English or Spanish to ensure compliance with cognitive testing and study visit procedures.
13. Provision of informed consent from the participant (or the participant's legally authorized representative (LAR) if unable to provide consent) and the study partner.

5.2 vMRI Assessments

Brain structural change is seen in normal aging, but is accelerated in neurodegenerative disease, including AD. Atrophy in AD arises from neuron and synapse loss that begins in the entorhinal cortex. The pathology then spreads throughout the limbic regions of the temporal lobe, including the hippocampal formation. Subsequently, neuron loss and atrophy is observed throughout neocortical association areas in temporal, parietal and frontal lobes.

vMRI allows the in vivo assessment of brain structure volume and provides a measure of atrophy rate. Results from vMRI studies suggest that the patterns of atrophy in AD, which mirror the pathological progression of the disease, can reliably be detected and tracked across time. Atrophy of the medial temporal lobe, including hippocampus and entorhinal cortex, has long been described in vMRI studies of AD. Hippocampal volume derived from MRI correlates with histological hippocampal volume and degree of neuronal loss and AD pathology, and entorhinal cortical thickness change appears to be an early and sensitive indicator of neurodegeneration associated with AD (Holland et al., 2009; Jack et al., 2004). Longitudinal MRI measures of regional and whole-brain volumetric change provide a valuable complement to cognitive measures in that they are not influenced by temporary symptomatic improvements, and they provide an early index of the study drug's ability to reach the target organ and have an effect on AD-related atrophy.

Participants will undergo vMRI scans of the brain at screening, week 24 and week 48 in order to assess for changes in brain volumes that may be associated with clinical change due to treatment with BHV-4157.

Volumetric MRI scans will use the same imaging protocol, which will include a localizer scan, a 3D T1weighted sagittal acquisition (MPRAGE or IR-SPGR), a T2-weighted FLAIR axial acquisition, a T2* gradient recalled echo axial acquisition for magnetic susceptibility, and a diffusion weighted axial acquisition to assess for restricted diffusion.

Images will be checked for image quality and adherence to scanning protocols. 3D T1-weighted datasets passing quality checks will be corrected for spatial distortion and for intensity variation. Screening and follow-up datasets for each participant will be spatially registered to one another using rigid-body registration followed by nonlinear registration and neuroanatomic parcellation to quantify whole-brain and subregional volumetric change on a patient-by patient basis.

The local MRI results will determine eligibility for each participant in the trial. It is the responsibility of the PI to make this determination following review of the MRI, and to sign as well as date the local report to acknowledge their review, and to confirm that the MRI results are consistent with AD and do not meet exclusion criteria. The PI is at liberty to consult with a local neuroradiologist, however there is no requirement for a formal MRI read from a neuroradiologist. The ADCS Medical Safety team, or ADCS Imaging core are available to address any questions surrounding MRI eligibility. If there are safety concerns are identified on this MRI, the PI should communicate with the participant's Primary Care Physician and consult with ADCS Medical Monitor, ADCS Director, and ADCS Imaging Core.

Whole brain volume (WBV, excluding cerebellum), bilateral ventricular volume and bilateral hippocampal volume will be measured. Quantitative anatomical regional change (Quarc) will be used as the computational MR image processing application. Detail for the statistical computations is given in the Statistical Analytical Plan (SAP).

If performed on the same day as a lumbar puncture, the vMRI should be conducted before the lumbar puncture. Otherwise, at least a 3-day window between vMRI and the lumbar puncture is required. Scanners that have passed the study's qualification procedures will be used. Participants must be scanned by the same scanner throughout the study.

Participants with a contraindication to MRI at the time of screening are deemed ineligible to participate in this study. Participants may continue to participate on the study if they have already been randomized but develop a contraindication to MRI during the course of the study.

5.3 CSF, Serum and Plasma Substudy Assessments

CSF, serum and plasma will be taken at screening within 14 days prior to first dose of study drug and within 14 days prior to weeks 24 and 48 to measure biomarkers (Aß42, Aß42/40 ratio, total tau, p-tau, neurogranin, NfL, YKL-40, VILIP, SNAP-25, sTREM2).

CSF samples should be collected at the same time of day, either morning (between 8 and 10 AM) or afternoon (between 1 and 3 PM). The first lumbar puncture must be conducted prior to initiation of study drug. Plasma samples for PK should be drawn at the time of lumbar puncture. Date and time of doses on the day of lumbar puncture and day prior should be collected in case report forms, for entry into the EDC system.

The estimated 100 participants (n=50 active, n=50 placebo) who are within the sentinel cohort that constitute the study sample for the futility analysis will also have the opportunity to participate in a CSF, serum, and plasma substudy, with samples drawn in the screening period and at week 24, with the option for a third sampling timepoint at week 48.

In addition to the sentinel substudy participants, other consenting trial participants will be approached to undergo a blood draw to provide serum and plasma biomarkers. For CSF, consenting participants will undergo a lumbar puncture at screening within 14 days prior to first dose of study drug and within 14 days prior to week 48 to measure the CSF biomarkers. Anti-platelet and anticoagulant medications and lumbar puncture are addressed above in in (Prohibited Concomitant Medications. Participants who are taking anticoagulants or dual antiplatelet drugs are excluded from the CSF substudy.

Details of the CSF Sampling are Contained in the Study Procedures Manual.

The unused portion of CSF may be transferred to the National Cell Repository for Alzheimer's Disease (NCRAD) for future research. Participants will be given the choice to allow such sample retention and further investigation of their CSF.

6 Study-Specific Instruments
6.1 Cognitive Measures
6.1.1 Alzheimer's Disease Assessment Scale Cognitive Subscale (ADAS-Cog 11)

The ADAS-Cog 11 (Rosen, Mohs, & Davis, 1984) is a structured scale that evaluates memory (word recall, word recognition), reasoning (following commands), language (naming, comprehension), orientation, ideational praxis (placing a letter in an envelope) and constructional praxis (copying geometric designs). Ratings of spoken language, language comprehension, word finding difficulty, and ability to remember test instructions are also obtained. The test is scored in terms of errors, with higher scores reflecting poorer performance and greater impairment. Scores can range from 0 (best) to 70 (worse).

6.1.2 Mini-Mental State Examination (MMSE)

The MMSE is a frequently used screening instrument for Alzheimer's disease drug trials. It evaluates orientation, memory, attention, concentration, naming, repetition, comprehension, and ability to create a sentence and to copy two intersecting pentagons (Folstein, Folstein, & McHugh, 1975). A lower score indicates more cognitive impairment. The highest (best) score is 30.

6.1.3 Montreal Cognitive Assessment (MoCA)

The MoCA is a brief mental status exam which was designed to be more sensitive to mild cognitive impairment and early dementia than the MMSE (Nasreddine et al., 2005). It assesses numerous cognitive domains, including attention and concentration, executive functions, memory, language, visuoconstructional skills, conceptual thinking, calculations, and orientation. Like the MMSE, the highest (best) score is 30. Administering both the MoCA and the MMSE in this trial will allow comparisons of the utility within the setting of a clinical trial.

6.1.4 Neuropsychological Test Battery (NTB)

The neuropsychological battery from the Uniform Data Set (v3.0—Form C2) of the National Alzheimer's Coordinating Center (NACC) (Weintraub et al., 2009) will be administered to provide a more detailed assessment of cognition. The battery includes brief measures of attention, processing speed, executive function, episodic memory, and language. Exploratory analyses will classify participants as typical (i.e., prominent memory impairment) or atypical (i.e., relative sparing of memory) based upon pattern of performance on the neuropsychological test battery at baseline. As described in the manual for test administration and scoring (Version 3.0, March 2015), Form C2 of the NACC UDS battery includes the following measures:

6.1.4.1 Craft Story 21 Recall (Immediate and Delayed)

This is a measure of verbal episodic memory (Craft et al., 1996). A brief story is read to the participant, who is then asked to retell it immediately from memory. The primary measure of performance is the number of story units recalled. Delayed recall of the story is assessed 20 minutes after immediate recall. Other neuropsychological measures are administered during the delay interval (Range: 0-25 for each recall trial).

6.1.4.2 Benson Complex Figure Copy & Recall

This test is a simplified form of the Rey-Osterrieth Complex Figure (Possin, Laluz, Alcantar, Miller, & Kramer, 2011). The purpose is to assess visuoconstructional and visual memory functions. In this test, the participant is presented with a figure composed of geometric shapes. The participant is then asked to reproduce (i.e. copy) the figure on the same page. The accuracy of each shape and its placement are recorded. The primary measure of performance is the total score for copying the figure (Range: 0-17). Approximately 10-15 minutes after the participant copies the figure, visual memory is assessed by asking the participant to draw the figure again, from memory, on a blank page. The accuracy of each shape and its placement are recorded. The primary measure of performance is the total score for the delayed drawing of the Benson figure (Range: 0-17).

6.1.4.3 Multilingual Naming Test (MINT)

The MINT is a test of visual confrontation naming (Ivanova, Salmon, & Gollan, 2013). Participants are required to identify (i.e. name) line drawings of objects. If the initial response is incorrect, semantic and/or phonemic cues are provided, as appropriate. Items are counted as correct if spontaneously named after semantic cuing (Range: 0-32).

6.1.4.4 Trail Making Test (Trails A and B)

The Trail Making Test is a test of processing speed and executive function. Trails A consists of 25 circles numbered 1 through 25 distributed over a white sheet of paper. The participant is instructed to draw a line to connect the circles in ascending numerical order as quickly as possible (150 second maximum). Trails B consists of 25 circles containing either numbers (1 through 13) or letters (A through L) that are randomly distributed across the page, and participants are instructed to connect the circles in alternating and ascending order (e.g., 1 to A; 2 to B). Performance is judged in terms of time to complete each trial. Time to complete Trails B (300 second maximum), adjusted for the time taken to complete Trails A to control for sensorimotor demands of the task, is a sensitive measure of executive function and working memory.

6.1.4.5 Verbal Fluency—Category Fluency

Category fluency assesses semantic memory and language fluency in which participants name as many different exemplars of a given semantic category as rapidly as possible. Participants will be given 60 seconds to name exemplars in each of two categories: animals and vegetables.

6.1.4.6 Verbal Fluency—Phonemic Fluency

Phonemic Fluency is a measure of word generation that may be sensitive to dysfunction in the dominant frontal lobe. Participants will be given 60 seconds to name exemplars that begin with each of the two letters: F and L.

6.1.4.7 Number Span Forward and Backward

Number Span assesses two different working memory constructs: Forward Number Span measures the capacity for retaining information very briefly for the purpose of repeating it exactly, while Backward Number Span measures the ability not only to retain the information but also to mentally manipulate the numbers and recite them in reverse sequence. Numbers for both forward and backward span tests are presented with sequences ranging from 2 to 9 numbers. Two trials are administered at each sequence length. Two scores are reported for each task: number of correct trials and longest sequence repeated correctly prior to failing two consecutive trials of the same length.

6.2 Behavioral and Functional Measures 6.2.1 Clinical Dementia Rating (CDR) Scale—Sum of Boxes (SOB)

The CDR-SOB (Hughes, Berg, Danziger, Coben, & Martin, 1982) is a validated composite rating of cognition and everyday functioning used in longitudinal AD research which incorporates both informant input and direct assessment of performance. It assesses through semi structured interview 3 cognitive domains including memory, orientation, and judgement/problem solving and 3 everyday functional domains including community affairs, home and hobbies and personal care. There are 5 levels of impairment from none CDR=0 to severe CDR=3. The individual domain scores are added to create a sum of the box scores.

6.2.2 ADCS-Activities of Daily Living (ADL) Scale

The ADCS-ADL scale is a questionnaire developed by the ADCS to assess functional performance in participants with AD (Galasko et al., 1997). Scores range from 0 to 75, with higher scores indicating better function.

6.2.3 Neuropsychiatric Inventory (NPI)

The NPI is a well-validated, reliable, multi-item instrument to assess psychopathology in AD dementia based on the results of an interview with the study partner (Cummings, 1997). The NPI evaluates both the frequency and severity of 10 neuropsychiatric features, including delusions, hallucinations, agitation/aggression, dysphoria, anxiety, euphoria, apathy, disinhibition, irritability and lability, and aberrant motor behavior, as well as evaluates sleep and appetite/eating disorders. Frequency assessments range from 1 (occasionally, less than once per week) to 4 (very frequently, once or more per day or continuously). Severity assessments range from 1 (mild) to 3 (severe). The score for each subscale is the product of severity and frequency and the total score is the sum of all subscales.

6.3 Modified Hachinski

This brief questionnaire, conducted by a clinician, incorporates information regarding medical history, cognitive symptoms and features of stroke, reported by a study partner as well as the neurological examination, and neuroimaging studies (Rosen, Terry, Fuld, Katzman, & Peck, 1980).

6.4 Sheehan Suicidality Tracking Scale (Sheehan STS)

The Sheehan STS (S-STS) is a prospective, patient self-reported or clinician administered rating scale that contains 16 questions to track both treatment-emergent suicidal ideation and behaviors (Sheehan, Alphs, et al., 2014; Sheehan, Giddens, & Sheehan, 2014). The S-STS will be completed on a paper form at the site. At the screening visit, the recall period for completing the S-STS is 12 months prior; at all other visits, the recall period for completing the S-STS is since the last visit. Subjects who have an S-STS score >0 should be evaluated by the investigator. If the investigator determines that a subject is at risk of suicide or self-harm, appropriate measures to ensure the subject's safety and obtain mental health evaluation must be implemented. The subject must immediately be discontinued from the study. The event should be recorded as either an AE or SAE as determined by the investigator and reported within 24 hours to the Sponsor.

Example 3

Capsules containing 140 mg of troriluzole for use in the studies described in Example 1 and Example 2 are prepared in the following proportions.

| Composition of Troriluzole Capsules, 140 mg | | |
|---|---|---|
| Component | Function | Content per Capsule |
| Drug Substance | Active ingredient | 140 mg |
| Mannitol | Binder/Filler | 60-90 mg |
| Microcrystalline cellulose + dicalcium phosphate[1] | Binder/Filler | 20-40 mg |
| Microcrystalline cellulose | Binder/Filler | 15-40 mg |
| Hydroxypropyl cellulose | Binder/Filler | 5-10 mg |
| Crospovidone | Disintegrant | 5-20 mg |
| Colloidal silicon dioxide | Glidant | 0.5-5 mg |
| Magnesium stearate (vegetable grade) | Lubricant | 0.5-5 mg |

[1]Provided as a 75:25 mixture of microcrystalline cellulose and anhydrous dicalcium phosphate.

Example 4

The T2 Protect AD trial has been conducted, which is a Phase 2/3, randomized, double-blind, placebo-controlled study evaluating the efficacy and safety of troriluzole in patients diagnosed with Alzheimer's disease of mild-to-moderate severity (Mini-Mental State Examination [MMSE] scores of 14-24; mild: 20-24, moderate: 14-19). The study data is summarized in Tables 1 to 6.

Troriluzole exhibited a numerical difference of a potential benefit at Week 48 on the neuropsychiatric inventory (NPI), an exploratory measure, in participants with mild-to-moderate AD. After 48 weeks, troriluzole treated participants (n=120) had a LS mean change from baseline of 2.3 points on the NPI score, versus 3.8 points for placebo treated (n=125) participants, [difference −1.5, 95% CI: −4.08, 1.10, p-value=0.258]. Troriluzole also exhibited numerical differences of a potential benefit at Week 48 on the NPI across subgroups, including analyses consisting of only mild AD patients, only moderate AD patients, only ApoE4 positive patients, and only ApoE4 negative patients. These findings are suggestive of a potential beneficial effect of troriluzole on reducing the frequency and severity of neuropsychiatric features in mild-to-moderate AD.

Moreover, a subgroup analysis consisting only of mild AD patients revealed that troriluzole exhibited numerical differences of a potential benefit at Week 48 on both the ADAS-cog co-primary measure, hippocampal volumetric MRI secondary measure, and NPI exploratory measure. After 48 weeks, troriluzole treated participants with mild AD (n=65) had a LS mean change from baseline of 4.2 points [95% CI: 2.7, 5.7] on the ADAS-Cog11 score, versus 4.9 points [95% CI: 3.4, 6.4] for placebo treated (n=63) participants, [difference 0.7, 95% CI: −1.4, 2.7, p-value=0.5233]. After 48 weeks, troriluzole treated participants with mild AD (n=48) had a LS mean percent deformation change from baseline hippocampal volume of −1.1% [95% CI: −1.6, −0.6] versus −1.6% [95% CI: −2.1, −1.0] for placebo treated (n=49) participants [difference −0.5%, 95% CI: −1.2, 0.3, p-value=0.2240]. After 48 weeks, troriluzole treated participants with mild AD (n=62) had a LS mean change from baseline of 2.1 points on the NPI score, versus 4.2 points for placebo treated (n=63) participants, [difference −2.1, 95% CI: −5.99, 1.78, p-value=0.286]. These findings are suggestive of a potential beneficial and/or disease-modifying effect of troriluzole including improving cognition, preserving hippocampal brain volumes, and reducing neuropsychiatric features in early stages of AD.

TABLE 1

Co-Primary ADAS-cog 11 at Week 48.

| Analysis Visit Type Statistic | Placebo | Troriluzole | Diference[1] |
|---|---|---|---|
| ADAS-Cog Total Score Week 48 Analysis Value | | | |
| N | 127 | 119 | |
| Mean (SD) | 32.4 (11.93) | 31.5 (10.82) | |
| Median | 30.0 | 30.0 | |
| Min, Max | 3.0, 64.0 | 8.0, 66.0 | |
| Change from Baseline | | | |
| N | 127 | 119 | |
| Mean (SD) | 6.1 (8.18) | 5.8 (7.40) | |
| Median | 5.0 | 6.0 | |
| Min, Max | −27.0, 43.0 | −10.0, 37.0 | |
| Model Estimates | | | |
| LSMean (SE) | 6.7 (0.68) | 6.7 (0.70) | 0.0 (0.93) |
| DF | | | 256.24 |
| 95% CI | (5.4, 8.1) | (5.3, 8.1) | (−1.8, 1.8) |
| P-Value | | | 0.9809 |

TABLE 2

Co-Primary ADAS-cog 11 at Week 48 (Mild AD Patients Only).

| Analysis Visit Type Statistic | Placebo | Troriluzole | Difference[1] |
|---|---|---|---|
| ADAS-Cog Total Score Week 48 Analysis Value | | | |
| N | 63 | 65 | |
| Mean (SD) | 26.4 (8.16) | 26.2 (8.22) | |
| Median | 26.0 | 26.0 | |
| Min, Max | 13.0, 56.0 | 8.0, 49.0 | |
| Change from Baseline | | | |
| N | 63 | 65 | |
| Mean (SD) | 5.0 (5.14) | 3.9 (5.90) | |
| Median | 5.0 | 4.0 | |
| Min, Max | −5.0, 20.0 | −10.0, 24.0 | |
| Model Estimates | | | |
| LSMean (SE) | 4.9 (0.77) | 4.2 (0.76) | 0.7 (1.02) |
| DF | | | 120.65 |
| 95% CI | (3.4, 6.4) | (2.7, 5.7) | (−1.4, 2.7) |

TABLE 3

Co-Primary CDR-SB at Week 48.

| Analysis Visit Type Statistic | Placebo | Troriluzole | Difference[1] |
|---|---|---|---|
| CDR01-Sum of Boxes Week 48 Analysis Value | | | |
| N | 127 | 118 | |
| Mean (SD) | 8.3 (3.05) | 8.3 (3.24) | |
| Median | 8.0 | 8.0 | |
| Min, Max | 2.0, 17.0 | 2.0, 17.0 | |
| Change from Baseline | | | |
| N | 127 | 118 | |
| Mean (SD) | 1.9 (2.38) | 1.9 (2.37) | |
| Median | 2.0 | 2.0 | |
| Min, Max | −8.0, 8.0 | −4.5, 8.5 | |
| Model Estimates | | | |
| LSMean (SE) | 1.9 (0.21) | 2.1 (0.21) | −0.2 (0.28) |
| DF | | | 260.40 |
| 95% CI | (1.5, 2.3) | (1.7, 2.5) | (−0.8, 0.3) |
| P-Value | | | 0.4474 |

TABLE 4

Co-Primary CDR-SB at Week 48 (Mild AD Patients Only).

| Analysis Visit Type Statistic | Placebo | Troriluzole | Difference[1] |
|---|---|---|---|
| CDR01-Sum of Boxes Week 48 Analysis Value | | | |
| N | 63 | 62 | |
| Mean (SD) | 7.1 (2.50) | 7.1 (2.79) | |
| Median | 7.0 | 6.5 | |
| Min, Max | 2.0, 12.0 | 2.0, 15.0 | |

TABLE 4-continued

Co-Primary CDR-SB at Week 48 (Mild AD Patients Only).

| Analysis Visit Type Statistic | Placebo | Troriluzole | Difference[1] |
|---|---|---|---|
| Change from Baseline | | | |
| N | 63 | 62 | |
| Mean (SD) | 1.5 (2.48) | 1.4 (2.06) | |
| Median | 1.0 | 1.0 | |
| Min, Max | −8.0, 7.5 | −4.5, 7.0 | |
| Model Estimates | | | |
| LSMean (SE) | 1.4 (0.30) | 1.7 (0.29) | −0.3 (0.40) |
| DF | | | 138.49 |
| 95% CI | (0.8, 1.9) | (1.1, 2.2) | (−1.1, 0.5) |
| P-Value | | | 0.4347 |

TABLE 5

Volumetric Hippocampal MRI at Week 48.

| Analysis Visit Type Statistic | Placebo | Troriluzole | Difference[1] |
|---|---|---|---|
| Hippocampal Volume Change Week 48 Analysis Value | | | |
| N | 90 | 87 | |
| Mean (SD) | −1.1 (1.92) | −1.1 (1.50) | |
| Median | −1.0 | −0.9 | |
| Min, Max | −6.4, 3.2 | −5.5, 1.9 | |
| Model Estimates | | | |
| LSMean (SE) | −1.1 (0.18) | −1.1 (0.18) | 0.0 (0.26) |
| DF | | | 174.00 |
| 95% CI | (−1.5, −0.8) | (−1.4, −0.7) | (−0.6, 0.5) |
| P-Value | | | 0.8670 |

TABLE 6

Volumetric Hippocampal MRI at Week 48 (Mild AD Patients Only).

| Analysis Visit Type Statistic | Placebo | Troriluzole | Difference[1] |
|---|---|---|---|
| Hippocampal Volume Change Week 48 Analysis Value | | | |
| N | 49 | 48 | |
| Mean (SD) | −1.6 (2.11) | −1.1 (1.61) | |
| Median | −1.3 | −0.9 | |
| Min, Max | −6.4, 3.2 | −5.5, 1.9 | |
| Model Estimates | | | |
| LSMean (SE) | −1.6 (0.27) | −1.1 (0.27) | −0.5 (0.38) |
| DF | | | 94.00 |
| 95% CI | (−2.1, −1.0) | (−1.6, −0.6) | (−1.2, 0.3) |
| P-Value | | | 0.2240 |

With regard to safety and tolerability, treatment with troriluzole at a dose of 280 mg once daily was relatively well tolerated and demonstrated a safety profile consistent with previous studies of troriluzole.

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, it is intended in accordance with the present invention that combination therapy using a riluzole prodrug and other therapeutic agents can be employed to treat ataxia and other associated diseases. Further, riluzole prodrugs other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A method of treating Alzheimer's Disease of mild to moderate severity in a patient in need thereof, the method comprising administering to the patient a riluzole prodrug having the following formula:

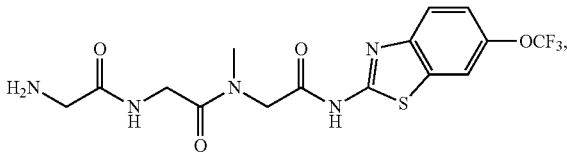 [SMILES: CN(CC(=O)Nc1nc2ccc(OC(F)(F)F)cc2s1)C(=O)CNC(=O)CN]

wherein the riluzole prodrug is administered to the patient at a dosage of 280 mg once per day or a dosage of 140 mg twice per day.

2. The method of claim 1, wherein the riluzole prodrug is administered to the patient in the form of a capsule.

3. The method of claim 1, wherein the riluzole prodrug is administered to the patient for a duration of from the onset of treatment to the end of the patient's life.

4. A method for improving a response in a patient afflicted with Alzheimer's disease of mild to moderate severity, the method comprising administering to the patient in need thereof, an effective amount of a riluzole prodrug having the following formula:

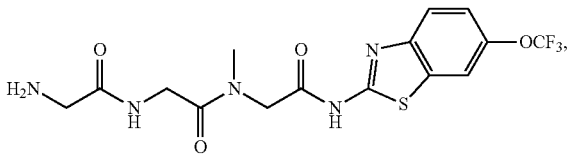 [SMILES: CN(CC(=O)Nc1nc2ccc(OC(F)(F)F)cc2s1)C(=O)CNC(=O)CN]

wherein the riluzole prodrug is administered to the patient at a dosage of 280 mg once per day or at a dosage of 140 mg twice per day.

5. The method of claim 4, wherein the improved response is one or more of overall survival, quality of life, overall response rate, duration of response, delay of onset, or patient reported outcome.

6. A kit for treating a patient afflicted with Alzheimer's Disease of mild to moderate severity, the kit comprising:
(a) a riluzole prodrug; and
(b) instructions for administering the riluzole prodrug in the method of claim 1,
wherein the riluzole prodrug has the following formula:

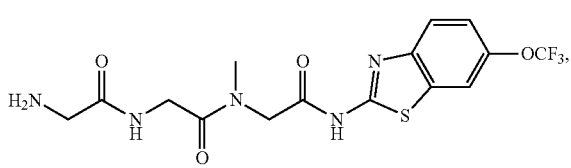 [SMILES: CN(CC(=O)Nc1nc2ccc(OC(F)(F)F)cc2s1)C(=O)CNC(=O)CN]

wherein a daily dosage of the riluzole prodrug in the kits is 280 mg.

7. A kit for improving a response in a patient afflicted with Alzheimer's Disease of mild to moderate severity, the kit comprising:
(a) a riluzole prodrug; and
(b) instructions for administering the riluzole prodrug in the method of claim 4,
wherein the riluzole prodrug has the following formula:

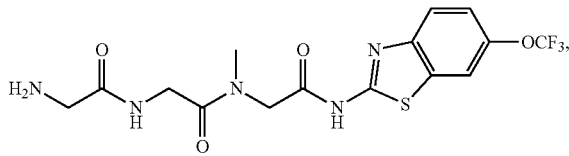 [SMILES: CN(CC(=O)Nc1nc2ccc(OC(F)(F)F)cc2s1)C(=O)CNC(=O)CN]

wherein a daily dosage of the riluzole prodrug in the kit is 280 mg.

* * * * *